United States Patent [19]

Aaltonen et al.

[11] Patent Number: 5,296,618
[45] Date of Patent: Mar. 22, 1994

[54] METHOD FOR THE MANUFACTURE OF THE DERIVATIVES OF PROPIONIC ACID

[75] Inventors: Olli Aaltonen, Helsinki; Veikko Komppa, Nummela; Martti Alkio, Espoo; Pekka Kairisalo, Helsinki; Martti Hytönen, Espoo; Anneli Hase, Helsinki, all of Finland

[73] Assignee: Orion-yhtymä Oy Fermion, Espoo, Finland

[21] Appl. No.: 58,125

[22] Filed: May 10, 1993

[30] Foreign Application Priority Data

May 14, 1992 [FI] Finland .................................. 922189

[51] Int. Cl.⁵ ................. C07D 301/32; C07D 303/12; C07D 303/22
[52] U.S. Cl. .................................. 549/542; 549/541; 549/549
[58] Field of Search .................... 549/542, 541, 549

[56] References Cited

U.S. PATENT DOCUMENTS

| | | | |
|---|---|---|---|
| 4,252,728 | 2/1981 | Delay | 549/549 |
| 4,430,339 | 2/1984 | Eistetter et al. | 549/549 |

FOREIGN PATENT DOCUMENTS

| | | |
|---|---|---|
| 0342903 | 11/1989 | European Pat. Off. |
| 0343714 | 11/1989 | European Pat. Off. |
| 0362556 | 4/1990 | European Pat. Off. |
| 0365029 | 4/1990 | European Pat. Off. |
| 0386654 | 9/1990 | European Pat. Off. |
| 3415035 | 10/1984 | Fed. Rep. of Germany |
| 120575 | 9/1980 | Japan ............... 549/549 |
| 60-013775 | 1/1985 | Japan . |
| 60-013776 | 1/1985 | Japan . |
| 61-145159 | 7/1986 | Japan . |
| 61-145160 | 7/1986 | Japan . |
| 62-212329 | 9/1987 | Japan . |
| 2110678 | 6/1983 | United Kingdom ............... 549/541 |
| WO89/10350 | 11/1989 | World Int. Prop. O. |
| WO90/04643 | 5/1990 | World Int. Prop. O. |

OTHER PUBLICATIONS

"Retention and Selectivity in Carbon Dioxide Supercritical Fluid Chromatography with Various Stationary Phases", P. Mourier, et al., Journal of Chromatography, 353 (1986) 61–75, Elsevier Science Publisher B.V., Amsterdam.

"Carbon Dioxide Supercritical Fluid Chromatography on a Chiral Diamide Stationary Phase for the Resolution of D– and L–Amino Acid Derivatives", Shoji Hara et al., Journal of Chromatography, 371 (1986) 153–158, Elsevier Science Publisher B.V., Amsterdam.

Primary Examiner—Joseph E. Evans
Attorney, Agent, or Firm—Burns, Doane, Swecker & Mathis

[57] ABSTRACT

A method is provided for supplying the desired optical isomer of a derivative of epoxypropionic acid from a racemix mixture. A representative derivative of epoxypropionic acid is an ester of (p-methoxyphenyl)epoxypropionic acid. The racemic mixture initially is dissolved in carbon dioxide and the resulting solution is passed through a chromatographic column. The desired isomer is subsequently separated from the resulting eluant. In a preferred embodiment the chromatographic column is packed with microcrystallized cellulosetriacetate, cellulose-tris-(3,5-dimethylphenylcarbamate), or cellulose-tris-(p-methylphenylcarbamate).

20 Claims, No Drawings

METHOD FOR THE MANUFACTURE OF THE DERIVATIVES OF PROPIONIC ACID

The object of this invention is a method for the manufacture of optically pure derivatives of epoxypropionic acid. The derivatives of epoxypropionic acid are important intermediates in the manufacture of some drug substances, 1,5-benzothiazepine, for example. The general structure of the derivatives of epoxypropionic acid is:

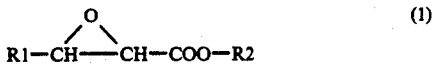
(1)

in which R1 and R2 are either H, alkylgroup or phenylgroup as such or substituted.

The derivatives of epoxypropionic acid can appear as different optically active space structures.

Usually only one of the optically active isomers of the final drug substance exhibits the desired effect. The other optical isomers are either ineffective or they may have harmful side effects. For that reason it is appropriate to aim to use and manufacture the drug substances as optically pure isomers.

The Patent Publication EP 342 903 comprises the separation of the enantiomers of 3-(4-methoxyphenyl)-epoxypropionic acid from each other by hydrolyzing first the ester of the racemic raw material and bringing the deglycidate thus obtained in touch with an optically active amine. The obtained diastereomeric salt is crystallized as optically pure, converted to an alkalic metal salt and alkylated to an optically pure ester. Also the Patent Publications EP 386 654, JP 61-145159 and JP 61-145160 comprise the corresponding resolution methods based on the formation of diastereomeric salt. These methods contain several phases, they last for many hours and various reagents and solvents are needed in them. They produce plenty of waste solutions, which are expensive to purify and which finally need to be destroyed.

The Patent Publication WO 89/10350 comprises the synthesis of the desired optically active derivative of epoxypropionic acid through sulfonate ester intermediate phase. Also this method contains numerous reagents and great amounts of different solvents, which need to be purified for reuse and the destruction of which has to be taken care for.

The Patent Publication EP 365 029 comprises the synthesis of the optically active epoxypropionic acids from the racemic dihalopropionic acid or chlorolactic acid by using as catalyst dehalogenase enzyme, that is separated from organism population grown in Pseudomonas geneva culture. The optically pure synthesis product is finally crystallized from the reaction mixture in several phases using many solvents. The enzymatically catalyzed synthesis requires a long reaction time, at least 12 hours, so the manufacturing rate of the method is very low.

The Patent Publications EP 362 556, EP 343 714 and WO 90/04643 comprise the separation of the enantiomers of the mixture of racemic epoxypropionic acid from each other by hydrolyzing their esters stereospecifically using enzymes, particularly lipases, as catalysts. Also these methods require vary long reaction times, even 48 hours. Many very dilute solutions, the purification, regeneration, destruction and handling of the waste water of which are expensive, are used in the methods for separation of enantiomers based on the enzymatic hydrolysis.

Finnish Patent Publication No. 911,264 discloses a technique for separating enantiomers wherein a solution containing a mixture of isomers is seeded with a crystal of the desired compound, crystals are allowed to form in the solution, and the resulting crystals are isolated. A preferred solvent is t-butylmethylether.

It is also known to synthesize optically active epoxypropionic acids or their derivatives by using L-aminoacid as starting material (JP 62212329) or other optically pure starting materials (JP 60013776, JP 60-13775). The method for synthesis contains many phases and many crystallizations from different solvents. Several reagents are used and lots of waste solutions are produced.

Surprisingly we have noticed, that the enantiomers of the derivatives of epoxypropionic acid can simply be separated from each other by dissolving the racemic mixture to be separated in carbon dioxide and leading the obtained solution through a chromatographic column.

The separation of enantiomers of the derivatives of epoxypropionic acid chromatographically by using carbon dioxide as mobile phase enables a simple, fast and in occupational and environmental safety points of view clean industrial manufacturing process for optically pure enantiomers of epoxypropionic acid.

One of the advantages of this invention is that the separation of enantiomers of the derivatives of epoxypropionic acid can be performed stepwise continuously so, that the time needed for separating one batch is short. The next separable batch of substance mixture can be charged to the chromatographic column soon after the previous one so that the outcoming, optically pure enantiomers will not get mixed to it. The separable batches of substance mixture can thus be typically charged to the chromatographic column at intervals of some minutes. This speeds up the purification process considerably in comparison with known methods. The benefit from large production rate is the drastic reduction of equipment sizes.

One of the advantages of this invention is also that the optical purity of the obtained enantiomers can be almost freely chosen and it can be optimized according to the requirements of the quality of the product and the economy.

Moreover it is an advantage, that the whole manufacturing process is simple. It contains only three main phases: the dissolving of the racemic mixture in carbon dioxide, the chromatographic separation of the enantiomers and the separation of the optically pure product from carbon dioxide. No reagents are needed and the whole purifying process can be performed by using only one solvent, carbon dioxide. Using only one solvent results the significant reduction of producing costs.

One advantage of the method is that carbon dioxide used as a solvent can very simply be recirculated for reuse. By reducing the pressure of carbon dioxide the optically pure derivatives of epoxypropionic acid precipitate and they can be simply separated from carbon dioxide by allowing carbon dioxide to evaporate under atmospheric pressure.

One advantage of the method is also that carbon dioxide does not leave any residues in the final product, as there always happens when using the previously known methods. Therefore the method according to this invention also advantageously improves the quality of the product.

Carbon dioxide separated from the product is evaporated and led after elevating the pressure and adjusting the temperature, to the dissolving of a new racemic, raw material batch. Due to the low heat of evaporation of carbon dioxide, the energy needed for recycling of carbon dioxide is only a fraction of the energy needed for redistillation of organic solvents. Therefore the method according to this invention brings significant reduction of producing costs.

One of the benefits of this invention is also that carbon dioxide used as a solvent is inexpensive, incombustible and non-toxic. This brings savings in explosion protection of the equipment and buildings and in controlling the hazards of solvent effluents. Thus the improved occupational safety is also an advantage of this method. The plant using carbon dioxide as a solvent does not cause harmful solvent effluents to the environment.

It is characteristic of the method according to this invention that the racemic derivative of epoxypropionic acid is dissolved in carbon dioxide under elevated pressure. The obtained solution is charged to the chromatographic column at 0°-120° C. temperature, most preferably at 30°-60° C. and under elevated pressure, most preferably 150-300 bar. The continuous eluant flow passes through the chromatographic column. The eluant is carbon dioxide, where a small amount of a modificator, most preferably 0.1-1 weight-%, most preferably small molecular alcohol or water, has been added to, if needed. The chromatographic column has been packed with solid packing material. The packing material has been prepared by coating suitable particles, most preferably silica gel particles, with suitable chiral materials, most preferably with cellulose esters or cellulose carbamates.

The composition of the eluant flow coming out from the chromatographic column is observed with a suitable detector and the flow is divided in successive parts so that one fraction contains the product, in other words the desired optical isomer of the derivative of epoxypropionic acid of the desired purity. The eluant flow coming out from the chromatographic column can further be divided, for example, into two fractions. The other fraction can still contain a considerable amount of the desired optical isomer and it can be returned to the racemic mixture to be charged to the column. The last fraction contains almost exclusively the non-desired optical isomer from the racemic mixture and it is removed.

Batches of the racemic derivatives of epoxypropionic acid dissolved in carbon dioxide are charged into the chromatographic column consecutively so that the more quickly eluting isomer of the batch will not get mixed with the slowest eluting isomer of the previous batch.

The pressure of the fractions of the eluant flowing out from the chromatographic column is reduced and/or the temperature is elevated so that the derivatives of epoxypropionic acid dissolved in them precipitate. Most preferably the eluant flow is allowed to expand adiabatically to the pressure of 50–60 bar. The precipitated derivatives of epoxypropionic acid are transferred with the eluant flow to pressure vessels where the carbon dioxide eluant is evaporated and the product is led into atmospheric pressure.

The carbon dioxide eluant evaporated in pressure vessels is led, after purifying and liquifying, if needed, to the inlet of the chromatographic column.

The following examples clarify the invention.

EXAMPLE 1

The racemic methyl ester of (p-methoxyphenyl)epoxypropionic acid was dissolved in carbon dioxide in pressure vessel at 40° C. under the pressure of 260 bar. The concentration of the dissolved ester in the carbon dioxide phase was 8 weight-%.

The carbon dioxide solution containing the methyl ester of (p-methoxyphenyl)epoxypropionic acid obtained from the dissolving vessel was conducted for ten seconds to the carbon dioxide flow, the temperature of which was 40° C. and the pressure 250 bar. The obtained mixture was led to the chromatographic column filled with silica gel particles coated with cellulose-tris-(3,5-dimethylphenylcarbamate).

Part of the eluant flow coming out from the chromatographic column was conducted continuously to the detector (FID). According to the signal given by flame ionization detector, the batch of the methyl ester of racemic (p-methoxyphenyl)epoxypropionic acid charged to the chromatographic column was divided in the column almost completely into two pure enantiomers, which came out from the column after 24 minutes and at intervals of 4 minutes.

EXAMPLE 2

The packing material of the chromatographic column and the conditions in the arrangements described in example 1 were varied. The methyl ester of (p-methoxyphenyl)epoxypropionic acid was still used as a separable racemic mixture.

| Experiment number | Temperature °C. | Pressure bar | Packing material of the column | Retention time of first peak min | Interval between the optical isomer peaks min |
|---|---|---|---|---|---|
| 1 | 120 | 100 | crown ether | 9 | 0 |
| 2 | 120 | 100 | brancod polysiloxane | 18 | 0 |
| 3 | 60 | 150 | microcrystalline cellulosetriacetate | 45 | 1 |
| 4 | 40 | 250 | microcrystalline cellulosetriacetate | 10 | 4 |
| 5 | 40 | 200 | cellulose-tris-(3,5-dimethyl-phenyl)carbamate | 40 | 6 |
| 6 | 35 | 300 | cellulose-tris-(p-methylphenyl)carbamate | 22 | 7 |

EXAMPLE 3

The arrangements described in example 1 were varied regarding to the eluant flow entering to the chromatographic column. Cellulose-tris-(3,5-dimethylphenylcarbamate) was used as packing material of the chromatographic column.

| Experiment number | Pressure bar | Temperature °C. | Retention time of the first eluating enantiomer min | Interval between the enantiomer peaks min |
|---|---|---|---|---|
| 7 | 180 | 40 | 48 | 8 |
| 8 | 200 | 40 | 40 | 6 |
| 9 | 250 | 40 | 23 | 4 |

-continued

| Experiment number | Pressure bar | Temperature °C. | Retention time of the first eluating enantiomer min | Interval between the enantiomer peaks min |
|---|---|---|---|---|
| 10 | 300 | 40 | 22 | 3 |
| 11 | 200 | 30 | 22 | 6 |
| 12 | 250 | 30 | 22 | 4 |
| 13 | 200 | 20 | 17 | 0 |

EXAMPLE 4

The arrangements described in example 1 were varied regarding to the amount of the racemic mixture charged to the chromatographic column.

| Experiment number | Amount of the charged rasemic mixture g/kg of the column's packing material | Retention time of the first eluating enantiomer min | Interval between the enantiomer peaks min | Measured resolution $R_M$ |
|---|---|---|---|---|
| 14 | 0.003 | 23 | 4 | 1.44 |
| 15 | 0.01 | 39 | 5 | 0.92 |
| 16 | 0.02 | 21 | 3 | 0.94 |
| 17 | 0.04 | 24 | 3 | 0.68 |
| 18 | 0.08 | 21 | 3 | 0.56 |
| 19 | 0.16 | 23 | 3 | 0.58 |
| 20 | 0.32 | 22 | 2 | 0.38 |
| 21 | 1 | 22 | 1.9 | 0.31 |
| 22 | 5 | 21 | 1.5 | 0.22 |
| 23 | 10 | 21 | 1.6 | 0.18 |

Resolution has been used as measure in evaluating the experimental results presented in example 4. The measured resolution Rs is the difference between the retention times of the eluted peaks divided with the bottom width of the latter eluting peak.

There is a certain dependance between the obtained resolution results and the amount of the charged racemic mixture in the experiments described in example 4. When the resolution is very low, the eluted peaks of the optically pure isomers almost overlap and the amount of the pure isomer obtained as product from the charged amount of racemic mixture is small. The economic manufacturing process requires that the resolution is at least in the range of 0.1–0.2.

We claim:

1. A method for the manufacture of optically active derivatives of epoxypropionic acid from racemic mixtures comprising, that
   a) the racemic mixture is dissolved in carbon dioxide and the obtained solution is conducted through a chromatographic column and
   b) the desired optical isomer of epoxypropionic acid is separated from the eluant.

2. The method according to the claim 1 comprising that the eluant containing carbon dioxide is led continuously to the chromatographic column.

3. The method according to claim 1 comprising, that the racemic derivative of epoxypropionic acid dissolved in the eluant containing carbon dioxide is conducted with continuous eluant flow to the chromatographic column periodically so that the amount of the racemic mixture batch charged to the column is at least 0.003 g per kg of the packing material of the column.

4. The method according to claim 1 comprising, that the eluant containing mainly carbon dioxide is conducted to the chromatographic column at the temperature of at least 0° C. and not more than 60° C.

5. The method according to claim 1 comprising, that the eluant containing mainly carbon dioxide is conducted to the chromatographic column under the pressure of at least 100 and not more than 400 atm.

6. The method according to the claim 1 comprising, that the pressure of each fraction of the eluant flow is reduced to not more than 60 atm so, that the derivative of epoxypropionic acid dissolved in each eluant flow precipitates.

7. The method according to the claim 1 comprising, that the racemic derivative of epoxypropionic acid is the ester of (p-methoxyphenyl)epoxypropionic acid.

8. The method according to the claim 1 comprising, that the chromatographic column is packed with the material manufactured of microcrystallized cellulosetriacetate.

9. The method according to the claim 1 comprising, that the chromatographic column is packed with the material made of cellulose-tris-(3,5-dimethylphenylcarbamate).

10. The method according to the claim 1 comprising, that the chromatographic column is packed with the material made of cellulose-tris-(p-methylphenylcarbamate).

11. The method according to the claim 1 comprising, that the eluant containing mainly carbon dioxide is conducted to the chromatographic column at the temperature of at least 30° C. and not more than 60° C.

12. The method according to the claim 1 comprising, that the eluant containing mainly carbon dioxide is conducted to the chromatographic column under the pressure of at least 150 and not more than 300 atm.

13. The method according to claim 2 comprising, that the eluant containing mainly carbon dioxide is conducted to the chromatographic column at the temperature of at least 0° C. and not more than 60° C.

14. The method according to claim 2 comprising, that the eluant containing mainly carbon dioxide is conducted to the chromatographic column under the pressure of at least 100 and not more than 400 atm.

15. The method according to claim 2 comprising, that the pressure of each fraction of the eluant flow is reduced to not more than 60 atm so, that the derivative of epoxypropionic acid dissolved in each eluant flow precipitates.

16. The method according to claim 2 comprising, that the racemic derivative of epoxypropionic acid is the ester of (p-methoxyphenyl) epoxypropionic acid.

17. The method according to claim 2 comprising, that the chromatographic column is packed with the material manufactured of microcrystallized cellulosetriacetate.

18. The method according to claim 2 comprising, that the chromatographic column is packed with the material made of cellulose-tris-(3,5-dimethylphenylcarbamate).

19. The method according to claim 2 comprising, that the chromatographic column is packed with the material made of cellulose-tris-(p-methylphenylcarbamate).

20. The method according to claim 2 comprising, that the eluant containing mainly carbon dioxide is conducted to the chromographic column at the temperature of at least 30° C. and not more than 60° C.

* * * * *